United States Patent
Schelwies et al.

(10) Patent No.: US 10,093,606 B2
(45) Date of Patent: Oct. 9, 2018

(54) METHOD OF PRODUCING FARNESYL ACETONE

(71) Applicant: BASF SE, Ludwigshafen (DE)

(72) Inventors: Mathias Schelwies, Heidelberg (DE); Rocco Paciello, Bad Dürkheim (DE); Heinz Eckhardt, Lambsheim (DE); Martine Dehn, Ludwigshafen (DE)

(73) Assignee: BASF SE (REITSTÖTTER, KINZEBACH & PARTNER), Ludwigshafen am Rhein (DE)

(*) Notice: Subject to any disclaimer, the term of this patent is extended or adjusted under 35 U.S.C. 154(b) by 0 days.

(21) Appl. No.: 15/307,081

(22) PCT Filed: Apr. 29, 2015

(86) PCT No.: PCT/EP2015/059329
§ 371 (c)(1),
(2) Date: Oct. 27, 2016

(87) PCT Pub. No.: WO2015/165959
PCT Pub. Date: Nov. 5, 2015

(65) Prior Publication Data
US 2017/0044084 A1    Feb. 16, 2017

(30) Foreign Application Priority Data

Apr. 30, 2014 (EP) .................................. 14166525

(51) Int. Cl.
C07C 45/69    (2006.01)
C07C 45/54    (2006.01)
C07C 45/62    (2006.01)

(52) U.S. Cl.
CPC .............. *C07C 45/69* (2013.01); *C07C 45/54* (2013.01); *C07C 45/62* (2013.01)

(58) Field of Classification Search
CPC .......... C07C 45/54; C07C 45/62; C07C 45/69
See application file for complete search history.

(56) References Cited

U.S. PATENT DOCUMENTS

| | | | | |
|---|---|---|---|---|
| 4,460,786 A | * | 7/1984 | Morel | ...................... B01J 31/24 560/174 |
| 4,621,165 A | * | 11/1986 | Morel | ................. C07C 7/14875 560/126 |
| 5,874,636 A | * | 2/1999 | Chabardes | ............ C07C 45/676 560/174 |

FOREIGN PATENT DOCUMENTS

| | | |
|---|---|---|
| DE | 69103175 T2 | 12/1994 |
| EP | 0034804 A2 | 9/1981 |
| EP | 0441708 A1 | 8/1991 |
| EP | 0806405 A1 | 11/1997 |
| WO | WO-2010046199 A2 | 4/2010 |

OTHER PUBLICATIONS

International Search Report for PCT/EP2015/059329 dated Jul. 1, 2015.
International Preliminary Report on Patentability dated Nov. 10, 2016 with English Translation.

* cited by examiner

*Primary Examiner* — Pancham Bakshi
*Assistant Examiner* — Mark R Luderer
(74) *Attorney, Agent, or Firm* — Drinker Biddle & Reath LLP

(57) ABSTRACT

The present invention relates to a process for preparing farnesyl acetone.

19 Claims, 9 Drawing Sheets

Figure 1:
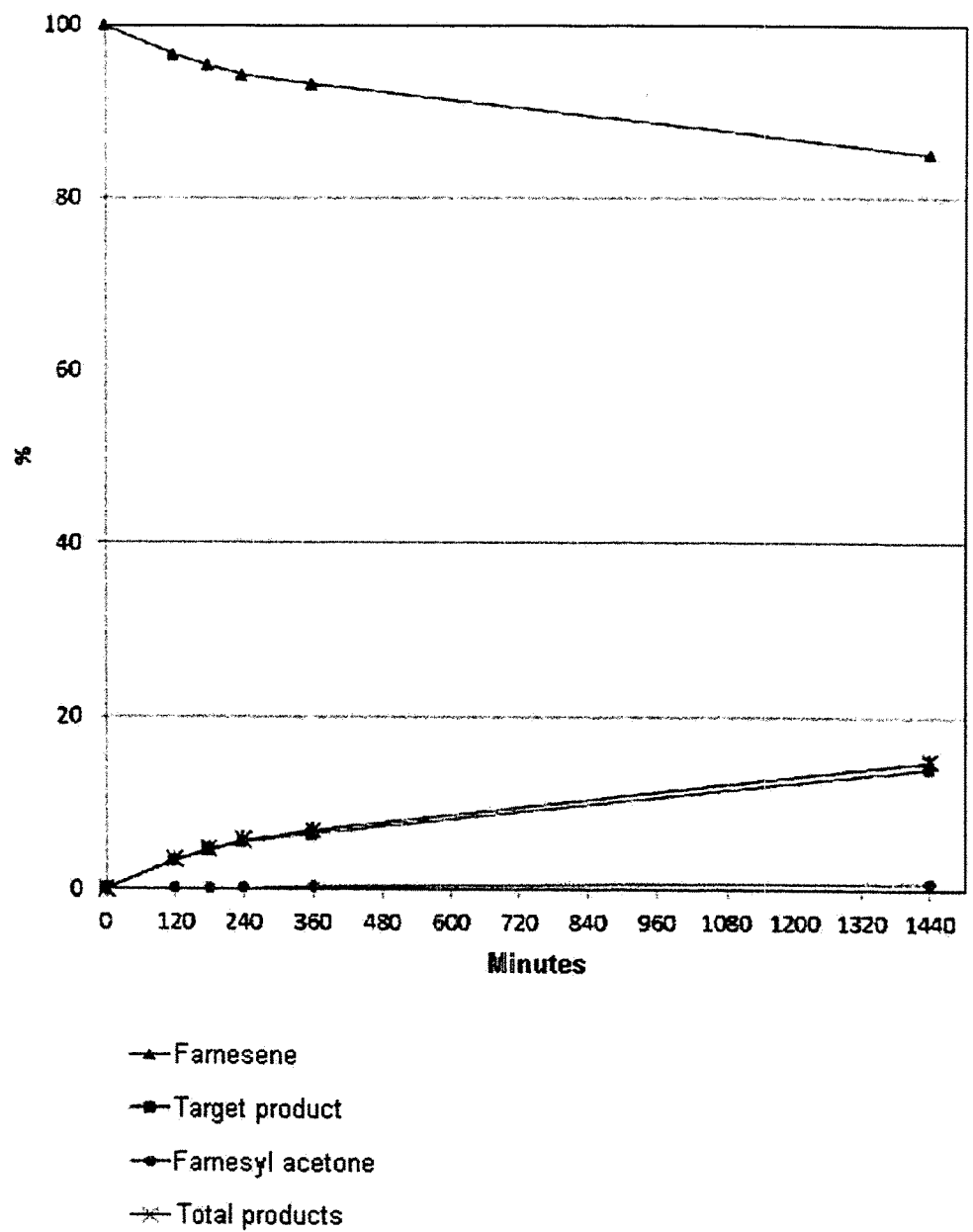

→▲— Farnesine
→■— Target product
→●— Farnesyl acetone
→✶— Total products

METHOD OF PRODUCING FARNESYL ACETONE

CROSS-REFERENCE TO RELATED APPLICATIONS

This application is a national stage application (under 35 U.S.C. § 371) of PCT/EP2015/059329, filed Apr. 29, 2015, which claims benefit of European Application No. 14166525.7, filed Apr. 30, 2014, both of which are incorporated herein by reference in their entirety.

BACKGROUND OF THE INVENTION

The present invention relates to a process for preparing farnesyl acetone.

PRIOR ART

Processes for preparing farnesyl acetone are known in the prior art.

Here, polyenes are reacted with methyl acetoacetate in the presence of a catalyst. The β-ketoester formed as reaction product is subjected to decarboxylation to give farnesyl acetone.

The polyenic ketone derivatives obtained are synthesis intermediates for the vitamin and perfume industry.

DE 69103175 T2 describes a process in which a 1,3-butadiene compound is reacted with an alkyl acetoacetate in the presence of a catalyst based on rhodium in water and a decarboxylation is carried out.

EP 0034804 A2 describes a process for preparing saturated terpenoid ketones, in particular hexahydrofarnesyl acetone, in the presence of palladium-comprising catalysts.

WO 2010/046199 describes a process for preparing gamma-delta-unsaturated ketones in the presence of ammonium salts as catalyst.

U.S. Pat. No. 4,621,165 describes a process in which mixtures of isoprenoid compounds are reacted with methyl acetoacetate in the presence of [RhCl(cycloocta-1,5-diene)]2, trisodium triphenylphosphinetrisulfonate in a solvent mixture of water and methanol are reacted as a water/alcohol mixture. These mixtures comprise farnesene as starting material, but large amounts of catalyst are used for the reaction.

U.S. Pat. No. 4,460,786 describes a process in which farnesene is reacted with ethyl acetoacetate in the presence of [RhCl(cycloocta-1,5-diene)]2, trisodium triphenylphosphinetrisulfonate in water.

Known processes for preparing farnesyl acetone are still in need of improvement and often have the disadvantage of long reaction times in large, bulky reactors and a costly use of large amounts of catalyst(s).

It is therefore an object of the present invention to provide an improved process for preparing farnesyl acetone, in which the abovementioned disadvantages are avoided. In particular, it should be possible to prepare farnesyl acetone in large amounts within a short time by means of this process. Furthermore, the reaction yield should be improved and the amounts of catalyst necessary for the reaction should be able to be reduced. Furthermore, the improved process should make it possible to prepare farnesyl acetone inexpensively and in reactors having a relatively small size.

SUMMARY OF THE INVENTION

It has now surprisingly been found that this object is achieved by a process according to claim 1.

The process of the invention for preparing farnesyl acetone is, compared to conventional processes, carried out in the presence of a solvent/water mixture with dispersion and in particular at a power input in the range from 0.1 to 5000 W/l.

The invention therefore provides a process for preparing keto compounds of the general formula (I)

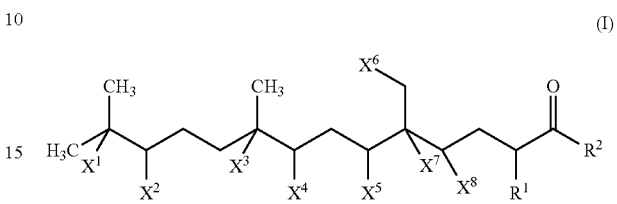

(I)

where
$R^1$ is hydrogen or a —C(O)O$R^3$ radical, where
  $R^3$ is $C_1$-$C_4$-alkyl;
$R^2$ is $C_1$-$C_4$-alkyl;
$X^1$ and $X^2$ are both hydrogen or together are the second bond of a double bond between the carbon atoms to which they are bound;
$X^3$ and $X^4$ are both hydrogen or together are the second bond of a double bond between the carbon atoms to which they are bound;
$X^5$, $X^6$, $X^7$, and $X^8$ are each hydrogen;
where one of the combinations of the radicals $X^5$ and $X^7$, $X^6$ and $X^7$ or $X^7$ and $X^8$ can also be the second bond of a double bond between the carbon atoms to which they are bound,
and isomers and mixtures thereof,
wherein
a) at least one farnesene compound of the general formula (II)

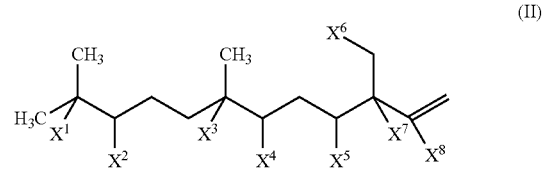

(II)

where
$X^1$ and $X^2$ together are the second bond of a double bond between the carbon atoms to which they are bound;
$X^3$ and $X^4$ together are the second bond of a double bond between the carbon atoms to which they are bound;
$X^5$ and $X^7$ together are the second bond of a double bond between the carbon atoms to which they are bound, with the proviso that $X^6$ is hydrogen; or
$X^6$ and $X^7$ together are the second bond of a double bond between the carbon atoms to which they are bound, with the proviso that $X^5$ is hydrogen, and
$X^8$ is hydrogen;
is subjected to a reaction with a β-keto ester of the general formula (III)

$R^2$—CO—CH$_2$—$R^1$ (III)

where
R¹ is a —C(O)OR³ radical, where R³ is $C_1$-$C_4$-alkyl;
in the presence of a catalyst and a solvent/water mixture, where the reaction mixture is subjected to dispersing using at least one mixer at a Reynolds number of greater than $10^4$,
to give a compound of the formula (I-a),

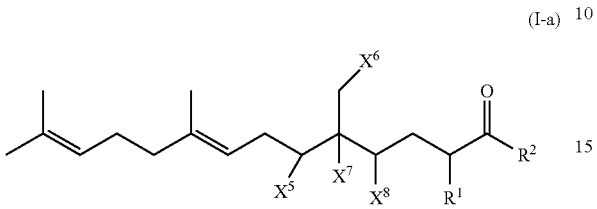

(I-a)

where
R¹ is a —C(O)OR³ radical,
where R³ is $C_1$-$C_4$-alkyl;
R² is $C_1$-$C_4$-alkyl;
X¹ and X² together are the second bond of a double bond between the carbon atoms to which they are bound;
X³ and X⁴ together are the second bond of a double bond between the carbon atoms to which they are bound;
one of the combinations of the radicals X⁵ and X⁷, X⁶ and X⁷ or X⁷ and X⁸ together is the second bond of a double bond between the carbon atoms to which they are bound and the remaining radicals X⁵, X⁶, X⁷ and X⁸ are each hydrogen;
and isomers and mixtures thereof;
b) the reaction mixture obtained in step a) is optionally subjected to a decarboxylation to give a compound of the formula (I-b),

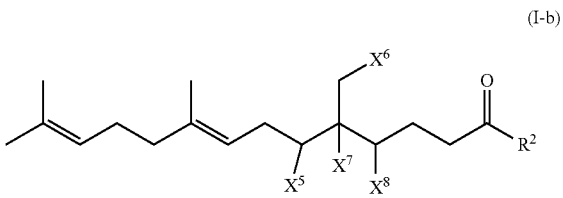

(I-b)

where
R² is $C_1$-$C_4$-alkyl;
one of the combinations of the radicals X⁵ and X⁷, X⁶ and X⁷ or X⁷ and X⁸ together is the second bond of a double bond between the carbon atoms to which they are bound and the remaining radicals X⁵, X⁶. X⁷ and X⁸ are each
and isomers and mixtures thereof,
c) the reaction mixture obtained in step b) is optionally subjected to a hydrogenation to give a compound of the formula (I-c)

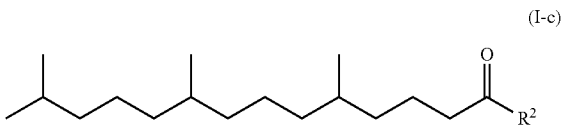

(I-c)

where
R² is $C_1$-$C_4$-alkyl.

The invention further provides for the use of farnesyl acetone obtainable by the process of the invention for preparing vitamin E, isophytol, dehydroisophytol, hexahydrofarnesyl acetone, tetrahydrofarnesyl acetone.

DETAILED DESCRIPTION OF THE INVENTION

For the purposes of the present invention, the term "alkyl" refers to straight-chain or branched $C_1$-$C_6$-alkyl and particularly preferably $C_1$-$C_4$-alkyl. Alkyl is in particular methyl, ethyl, n-propyl, isopropyl, n-butyl, isobutyl (2-methylpropyl), sec-butyl (1-methylpropyl), tert-butyl (1,1-dimethylethyl), n-pentyl or n-hexyl. Alkyl is especially methyl, ethyl, n-propyl, isopropyl or isobutyl, in particular methyl.

Unless indicated more precisely in the following, the term "farnesene compound" refers for the purposes of the invention to α-farnesene (3,7,11-trimethyl-1,3,6,10-dodecatetraene) in pure form, β-farnesene (7,11-dimethyl-3-methylene-1,6,10-dodecatriene) in pure form and also a mixture of α-farnesene and β-farnesene of any composition. The term farnesene compound also refers to mixtures of the isomers of α-farnesene, mixtures of the isomers of β-farnesene or an isomer of α-farnesene or β-farnesene in pure form. There are four isomers of α-farnesene, namely (3E,6E)-3,7,11-trimethyl-1,3,6,10-dodecatetraene, (3Z,6Z)-3,7,11-trimethyl-1,3,6,10-dodecatetraene, (3Z,6E)-3,7,11-trimethyl-1,3,6,10-dodecatetraene and (3E,6Z)-3,7,11-trimethyl-1,3,6,10-dodecatetraene. There are two isomers of β-farnesene, namely (6E)-7,11-dimethyl-3-methylene-1,6,10-dodecatriene and (6Z)-7,11-dimethyl-3-methylene-1,6,10-dodecatriene. If mention is made in the following of β-farnesene of the formula (IIA), only one isomer is depicted.

Unless indicated more precisely in the following, the term "farnesyl acetone" of the formula (I-aA) refers for the purposes of the invention to 6,10,14-trimethylpentadeca-5,9,13-trien-2-one in pure form, 6,10,14-trimethylpentadeca-6,9,13-trien-2-one in pure form, 10,14-dimethyl-6-methylenepentadeca-9,13-trien-2-one in pure form and a mixture of the isomers of 6,10,14-trimethylpentadeca-5,9,13-trien-2-one, 6,10,14-trimethylpentadeca-6,9,13-trien-2-one and 10,14-dimethyl-6-methylenepentadeca-9,13-trien-2-one in any composition. The term farnesyl acetone of the formula (I-aA) also refers to mixtures of 6,10,14-trimethylpentadeca-5,9,13-trien-2-one or an isomer thereof in pure form, mixtures of 6,10,14-trimethylpentadeca-6,9,13-trien-2-one or an isomer thereof in pure form and mixtures of 10,14-dimethyl-6-methylenepentadeca-9,13-trien-2-one or an isomer thereof in pure form. There are four isomers of 6,10,14-trimethylpentadeca-5,9,13-trien-2-one, namely (5E,9E)-6,10,14-trimethylpentadeca-5,9,13-trien-2-one (E,E-farnesyl acetone), (5Z,9Z)-6,10,14-trimethylpentadeca-5,9,13-trien-2-one (Z,Z-farnesyl acetone), (5Z,9E)-6,10,14-trimethylpentadeca-5,9,13-trien-2-one (Z,E-farnesyl acetone) and (5E,9Z)-6,10,14-trimethylpentadeca-5,9,13-trien-2-one. There are four isomers of 6,10,14-trimethylpentadeca-5,9,13-trien-2-one, namely (6E,9E)-6,10,14-trimethylpentadeca-6,9,13-trien-2-one, (6Z,9Z)-6,10,14-trimethylpentadeca-6,9,13-trien-2-one, (6E,9Z)-6,10,14-trimethylpentadeca-6,9,13-trien-2-one and (6Z,9E)-6,10,14-trimethylpentadeca-6,9,13-trien-2-one. There are two isomers of 10,14-dimethyl-6-methylenepentadeca-9,13-trien-2-one, namely (9E)-10,14-dimethyl-6-methylenepentadeca-9,13-trien-2-one and (9Z)-10,14-dimethyl-6-methylenepentadeca-9,13-trien-2-one.

For the purposes of the present invention, the terms "trans" and "E" are used synonymously, in particular as "trans-β-farnesene" and "β-E-farnesene", unless indicated otherwise.

If farnesyl acetone of the formulae (I-aA) or (I-aA1) is mentioned in the following, only one isomer is depicted.

For the purposes of the present invention, the expression "keto compounds of the general formula (I) and isomers and mixtures thereof" refers to keto compounds of the general formula (I) and isomers of the compounds of the general formula (I) and mixtures of the compounds of the general formula (I) and isomers thereof.

For the purposes of the present invention, dispersing refers to the mixing of at least two materials which without energy input do not dissolve in one another or sparingly dissolve in one another. During dispersing, one material (disperse phase) is distributed in another material (continuous phase). In the present case, the objective is to produce an emulsion (liquid/liquid). An interfacial tension arises at the interface between the two phases and prevents a dispersion from being formed spontaneously. The energy input during dispersing breaks up the liquid droplets, resulting in equalization in the region of the phase boundaries. This brings about temporary stability of the dispersion. The objective of a dispersing operation is enlargement of phase interfaces so that, for example, chemical reactions can proceed more quickly.

For the purposes of the present invention, a mixer is a rotor-stator stirring system, a stirrer/stirring device selected from among cross-beam stirrers, mesh stirrers, blade stirrers, anchor stirrers, helical stirrers, MIG stirrers, disk stirrers, propeller stirrers, impeller stirrers, half-moon stirrers and combinations thereof.

The process of the invention has the following advantages:
- the power input required for dispersing is smaller compared to conventional processes,
- the required use of catalyst for the reaction is smaller compared to conventional processes,
- the space-time yield is greater compared to conventional processes,
- the conversion of the starting material in the process of the invention in the presence of an ethanol/water mixture is more than twice as high compared to a conventional process using water.

Step a)

Suitable farnesene compounds for the use in step a) can comprise at least one β-farnesene compound of the formula (IIA)

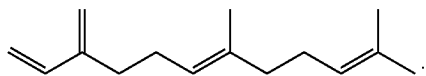

(IIA)

In a preferred embodiment, the farnesene compound of the formula (II) comprises at least one β-farnesene compound of the formula (IIA) in an amount of at least 70% by weight, in particular at least 80% by weight, very particularly preferably at least 90% by weight, based on the total weight of the farnesene compound of the formula (II).

Preference is given to the β-farnesene compound β-E-farnesene ((6E)-7,11-dimethyl-3-methylene-1,6,10-dodecatriene).

In a further preferred embodiment, a mixture of an α-farnesene compound and a β-farnesene compound is used in step a). A mixture of α-farnesene compound and β-farnesene compound, preferably β-E-farnesene, in any composition is suitable.

Suitable farnesene compounds for use in step a) can also comprise at least one α-farnesene compound, in essentially pure form. For the purposes of the present invention, essentially pure form means that the farnesene compound used in step a) preferably consists to an extent of at least 70% by weight, particularly preferably at least 80% by weight, in particular at least 90% by weight, based on the total weight of the farnesene compound, of an α-farnesene compound of the general formula (II).

Preference is given to using methyl acetoacetate or ethyl acetoacetate as β-keto ester of the general formula (III) in step a).

The reaction in step a) is carried out in the presence of a catalyst and a solvent/water mixture, with the reaction mixture being subjected to dispersing using at least one mixer at a Reynolds number of greater than $10^4$.

Suitable catalysts are, for example, the catalysts described in U.S. Pat. No. 4,621,165 or in EP 0441708.

In a preferred embodiment, the catalyst is prepared in situ. However, the catalyst can, if desired, also be prepared separately and isolated by conventional methods. To prepare the catalyst in situ, at least one compound or a complex of a transition metal of group 9 of the Periodic Table can be reacted with a water-soluble phosphine. A catalyst prepared in this way is generally able to dissolve in water under the reaction conditions. The compound or complex of a transition metal of group 9 of the Periodic Table is preferably a rhodium compound or a rhodium complex.

Suitable rhodium compounds or complexes are, for example, rhodium(I), rhodium(II) and rhodium(III) salts, e.g. rhodium(III) chloride, rhodium(III) bromide, rhodium(III) nitrate, rhodium(III) sulfate, rhodium(II) or rhodium(III) oxide, rhodium(II) or rhodium(III) acetate, rhodium(II) or rhodium(III) carboxylate, $Rh(CH_3COCH_2COCH_3)_3$, dicarbonyl-rhodium acetylacetonate, $[RhCl(cyclooca-1,5-diene)]_2$, $[RhCl(C_2)_2]_2$ and $RhCl_3(C_2H_5NH_2)_3$. Preference is given to using $[RhCl(cyclooca-1,5-diene)]_2$.

Suitable phosphine compounds are alkali metal, alkaline earth metal, ammonium or quaternary ammonium salts of (para-sulfonatophenyl)diphenylphosphine; (meta-sulfonato-para-methylphenyl)di(para-methylphenyl)phosphine; (meta-sulfonato-para-methoxyphenyl)di(para-methoxyphenyl)phosphine; (meta-sulfonato-para-chlorophenyl) di(para-chlorophenyl)phosphine; di(para-sulfonatophenyl)phenylphosphine; di(meta-sulfonato-para-methylphenyl)(para-methylphenyl)phosphine; di(meta-sulfonato-para-methoxymethyl)(para-methoxyphenyl)phosphine; di(meta-sulfonato-para-chlorophenyl) (para-chlorophenyl) phosphine; tri(para-sulfonatophenyl) phosphine; tri(meta-sulfonato-phenyl)phosphine, tri(meta-sulfonato-para-methylphenyl) phosphine; tri(meta-sulfonato-para-methoxyphenyl)phosphine; tri(meta-sulfonato-para-methoxyphenyl) phosphine; tri(meta-sulfonato-para-chlorophenyl)phosphine; (ortho-sulfonato-para-methylphenyl)(meta-sulfonato-para-methyl)(meta,meta'-disulfonato-para-methyl) phosphine; and (meta-sulfonatophenyl)(meta-sulfonato-para-chlorophenyl) (meta,meta'-disulfonato-para-chlorophenyl)phosphine. Preference is given to using tri(sodium-meta-sulfonatonatophenyl) phosphine.

The phosphine compound and the rhodium compound or the rhodium complex are usually employed in a molar ratio of from about 1:1 to 50:1, preferably from 1:1 to 30:1, in particular from 1:1 to 25:1.

Step a) is usually carried out under a protective gas atmosphere.

The process for preparing farnesyl acetone of the formula (I-aA),

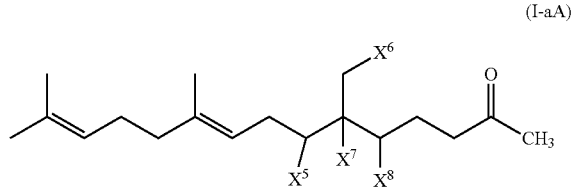

where one of the combinations of the radicals $X^5$ and $X^7$, $X^6$ and $X^7$ or $X^7$ and $X^8$ together is the second bond of a double bond between the carbon atoms to which they are bound and the remaining radicals $X^5$, $X^6$, $X^7$ and $X^8$ are each hydrogen, and isomers and mixtures thereof, preferably comprises the steps a) and b).

The process for preparing hexahydrofarnesyl acetone (6,10,14-trimethyl-2-pentadecanone) of the formula (I-bB),

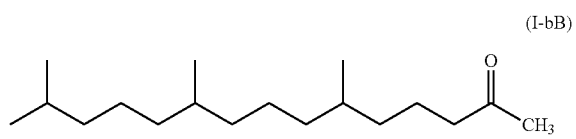 [SMILES: CC(=O)CCCC(C)CCCC(C)CCCC(C)C]

preferably comprises the steps a), b), and c).

The solvent of the solvent/water mixture is preferably selected from among $C_1$-$C_5$-alkanols, in particular methanol, ethanol, n-propanol, isopropanol, n-butanol and t-amyl alcohol; $C_2$-$C_6$-dialkanols, in particular monoethylene glycol and diethylene glycol, saturated cyclic ethers, in particular tetrahydrofuran (THF) and dioxane, saturated acyclic ethers such as methyl tert-butyl ether, 1,2-dimethoxyethane, diethylene glycol dimethyl ether, triethylene glycol dimethyl ether, nitriles such as acetonitrile, saturated ketones such as acetone, esters of saturated $C_1$-$C_6$-monocarboxylic acids with $C_1$-$C_6$-alkanols, e.g. methyl acetate, ethyl acetate, $C_1$-$C_6$-alkylamides and di-$C_1$-$C_6$-alkylamides of saturated $C_1$-$C_6$-monocarboxylic acids, e.g. dimethylformamide, lactams such as N-methylpyrrolidone and mixtures thereof.

The solvent/water mixture is preferably present in a volume ratio of preferably from 1:5 to 5:1, particularly preferably from 2:1 to 1:2, very particularly preferably 1:1, in each case calculated as pure material.

In general, step a) is carried out in the presence of a base. Suitable bases are alkali metal and alkaline earth metal hydroxides, alkali metal and alkaline earth metal hydrogencarbonates, alkali metal and alkaline earth metal carbonates, alkali metal phosphates or alkali metal alkanolates of $C_1$-$C_6$-alkanols. Preference is given to using alkali metal hydroxides such as sodium hydroxide or potassium hydroxide, alkali metal carbonates such as sodium carbonate or potassium carbonate, alkali metal hydrogencarbonates such as sodium hydrogencarbonate or potassium hydrogencarbonate, alkali metal phosphates such as $Na_3PO_4$ or $K_3PO_4$ or alkali metal alkanolates such as sodium methoxide, sodium ethoxide, sodium propoxide, sodium butoxide, potassium methoxide, potassium ethoxide or potassium butoxide as base.

Particular preference is given to using sodium carbonate, potassium carbonate and sodium phosphate. Very particular preference is given to using sodium carbonate.

In a specific embodiment, step a) is carried out in the presence of sodium carbonate. The dispersing in step a) is preferably carried out at a power input in the range from preferably 0.1 to 5000 W/l, particularly preferably from 10 to 600 W/l, very particularly preferably from 20 to 100 W/l.

For the purposes of the present invention, the power input of the stirrers used is determined experimentally as described below, as shown, in particular, in examples E1 and E2.

For rotor-stator stirring systems:

In the case of a rotor-stator stirring system, an initial amount of a system to be stirred, comprising one or more phase(s) and a density is placed in an adiabatic stirring vessel and the rotor-stator stirring system is arranged in the stirring vessel. The initial temperature of the system to be stirred is measured, the rotor-stator stirring system is started and the temperature change on introduction of shear forces into the system to be stirred by the rotor-stator stirring system is measured over a stirring time t at a rotational speed n of the rotor-stator stirring system. In addition, the final temperature of the system to be stirred is measured. Using the measured data the specific power input in the system to be stirred is calculated. The following calculations are carried out for the example of water as system to be stirred.

The power input is calculated according to formula 1:

$$P = [(mW_{transverse} * cpW_{transverse} * \Delta T) + (\Delta mW * \Delta H_{transverse})]/t, \quad \text{formula 1:}$$

where P is the volume-specific power input in watt, $mW_{transverse}$ is the average amount of water in kg, $cPW_{transverse}$ is the average heat capacity of water in kJ/(kg*K), $\Delta T$ is the difference between initial and final temperature of the water in °C., $\Delta mW$ is the difference between initial and final amount of water in kg, $\Delta H_{transverse}$ is the average enthalpy of vaporization of water in kJ/kg and t is the stirring time in s.

Using the power input P determined in the formula 1, the dimensionless Newtonian power index Ne is calculated according to formula 2:

$$Ne = P/(\rho W * n^3 * d_2^5), \quad \text{formula 2:}$$

where P is the volume-specific power input in watt, $\rho W$ is the density of water in kg/m³, n is the rotational speed of the stirrer in s⁻¹ and $d_2$ is the diameter of the stirring device nm.

In a turbulent flow regime in the stirrer systems, the Ne number is virtually constant. The dimensionless Reynolds number is determined using the formula 3 below.

$$Re = n * d_2^2 * (\rho/\eta), \quad \text{Formula 3:}$$

where n is the rotational speed of the stirrer in s⁻¹, $d_2$ is the diameter of the stirring device in m, $\rho$ is the density of the system to be stirred in kg/m³ and $\eta$ is the dynamic viscosity of the system to be stirred in Pa·s.

For flow systems in which stirrers are used, turbulent flow in the range of Reynolds numbers greater than 1000 can be assumed.

Using formula 4 below, the power input determined for water using the formula 1 is applied to a specific system to be stirred having a specific density and the specific power Ps is thus determined:

$$Ps/P = Ne * (\rho s * n^3 * d_2^5)P, \quad \text{formula 4:}$$

where Ps is the specific power in watt, P is the volume-specific power input in watt, Ne is the dimensionless Newtonian power index, ρs is the specific density of the specific system to be stirred in kg/m³ and d₂ is the diameter of the stirring device in m.

For systems with stirring devices (stirrer systems):

A stirring device can, for example, be a half-moon stirrer. At a given rotational speed n in min⁻¹, the torque M in Ncm⁻¹ is measured in the reaction product.

The power is calculated according to formula 5 below, as follows:

$$Ps = M*2*pi*n, \qquad \text{formula 5:}$$

where Ps is the specific power in watt, M is the torque in Ncm⁻¹ and n is the rotational speed in min⁻¹.

The volume-specific power input Ps in watt is calculated on the basis of the volume of the system to be stirred.

For the purposes of the present invention, stirring is, in particular, mixing, internal mixing, homogenization, dispersing, suspending, emulsification.

A stirrer is preferably also referred to as stirring device and is selected from among cross beam stirrers, mesh stirrers, blade stirrers, anchor stirrers, helical stirrers, MIG stirrers, disk stirrers, propeller stirrers, impeller stirrers, half-moon stirrers and combinations thereof.

Dispersing in step a) is preferably effected using a stirrer at a circumferential velocity in the range from 1 to 80 m/s, preferably in the range from 1.8 to 30 m/s.

Dispersing in step a) is preferably carried out at a temperature in the range from preferably 50 to 200° C., more preferably from 60 to 150° C., particularly preferably from 70 to 120° C., very particularly preferably in the range from 80 to 100° C.

In conventional processes, the compound of the formula (I-a) obtained in step a) and isomers and mixtures thereof can be isolated from the reaction mixture. In general, the reaction mixture obtained in step a) can be used for the subsequent reactions without further purification.

Step b)

In a first embodiment, step b) comprises alkyl decarboxylation or hydrolysis/decarboxylation of the reaction mixture obtained in step a) at elevated temperatures.

In a second embodiment, step b) comprises alkyl decarboxylation or hydrolysis/decarboxylation of the compound of the formula (I-a) and isomers and mixtures thereof at elevated temperatures in a solvent/water mixture. Suitable solvent/water mixtures are the solvent/water mixtures mentioned in step a).

Step b) is usually carried out in the presence of a salt. Suitable salts comprise alkali metal and alkaline earth metal carbonates such as sodium carbonate or potassium carbonate, alkali metal halides such as lithium chloride, lithium iodide, sodium chloride, sodium bromide or sodium iodide, potassium chloride, alkaline earth metal halides and alkali metal phosphates such as sodium phosphate or potassium phosphate.

Step b) is usually carried out at a temperature in the range from 50 to 250° C., preferably from 100 to 200° C., in particular from 120 to 200° C.

It can be advantageous to carry out step b) in an autoclave.

In a preferred embodiment of the process of the invention, steps a) and b) are carried out in one operation (one-pot reaction), i.e. without isolation of the compound of the formula (I-a), isomers and mixtures thereof.

Step c)

Suitable hydrogenation catalysts are supported palladium catalysts. Suitable supports include many materials, for example aluminum oxide, ceramic support materials or carbon or graphite. Support materials for these catalysts are known to those skilled in the art and are generally used in finely divided form, which can optionally be pressed to give pellets. Particular preference is given to using carbon, in particular activated carbon, as support material. Preference is likewise given to using aluminum oxide as support material. Very particular preference is given to using palladium on carbon (10%).

The hydrogenation is usually carried out in a solvent. Suitable solvents comprise cyclic ethers such as tetrahydrofuran (THF) or dioxane or alkanols such as methanol or ethanol.

Step c) is usually carried out at a temperature of from 20 to 100° C.

The reaction is preferably carried out in an autoclave. The hydrogenation is usually carried out at a hydrogen pressure of from 0.5 to 20 bar, preferably from 0.5 to 15 bar and particularly preferably from 1 to 12 bar.

As regards more precise details on the subject of catalytic hydrogenations of polyene compounds, reference is made to EP 34804.

One specific embodiment of the process of the invention is a process for preparing farnesyl acetone of the formula (I-aA),

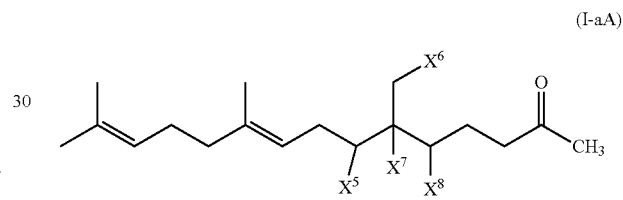

isomers and mixtures thereof,
where
one of the combinations of the radicals X⁵ and X⁷, X⁶ and X⁷ or X⁷ and X⁸ together is the second bond of a double bond between the carbon atoms to which they are bound and the remaining radicals X⁵, X⁶, X⁷ and X⁸ are each hydrogen,
wherein the process comprises the steps a) and b), Especial preference is given to a process for preparing farnesyl acetone of the formula (I-aA.1)

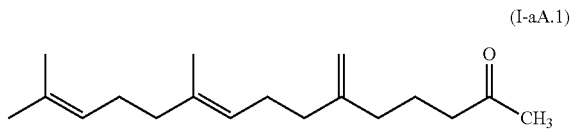 [SMILES: C=C(CC/C=C(\C)CCC=C(C)C)CCCC(C)=O]

and isomers and mixtures thereof comprising the steps a) and b) of the process of the invention, wherein the farnesene compound of the formula (II) in step a) is β-E-farnesene to an extent of at least 70% by weight, preferably at least 80% by weight and in particular at least 90% by weight, and the β-keto ester of the general formula (III) is methyl acetoacetate.

In a further preferred embodiment, a mixture of β-farnesene and α-farnesene is used as farnesene compound of the formula (II) in step a) and methyl acetoacetate is used as β-keto ester of the general formula (III). The reaction is carried out in the presence of sodium carbonate.

The steps a) and b) of the process of the invention make it possible to prepare farnesyl acetone, which is an important intermediate for the preparation of hexahydrofarnesyl acetone, in a simple manner and on an industrial scale in an advantageous way.

Especial preference is likewise given to a process for preparing hexahydrofarnesyl acetone (6,10,14-trimethyl-2-pentadecanone) of the formula (I-bB.1),

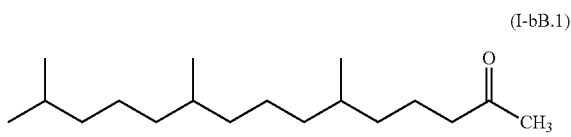 [SMILES: CC(=O)CCCC(C)CCCC(C)CCCC(C)C]

(I-bB.1)

comprising the steps a), b) and c) of the process of the invention, wherein the farnesene compound of the formula (II) in step a) is β-E-farnesene and the β-keto ester of the general formula (III) is methyl acetoacetate. In a further preferred embodiment, the farnesene compound of the formula (II) used in step a) is a mixture of β-farnesene and α-farnesene and the β-keto ester of the general formula (III) is methyl acetoacetate.

The steps a), b) and c) of the process of the invention make it possible to prepare hexahydrofarnesyl acetone, which is an important intermediate for the preparation of phytol and isophytol and thus for the preparation of vitamin E, in a simple manner and on an industrial scale in an advantageous way.

DESCRIPTION OF FIGURES AND EXAMPLES

The invention is illustrated below by FIGS. 1 to 9 and the associated examples A1 to E1.

Figure 2:
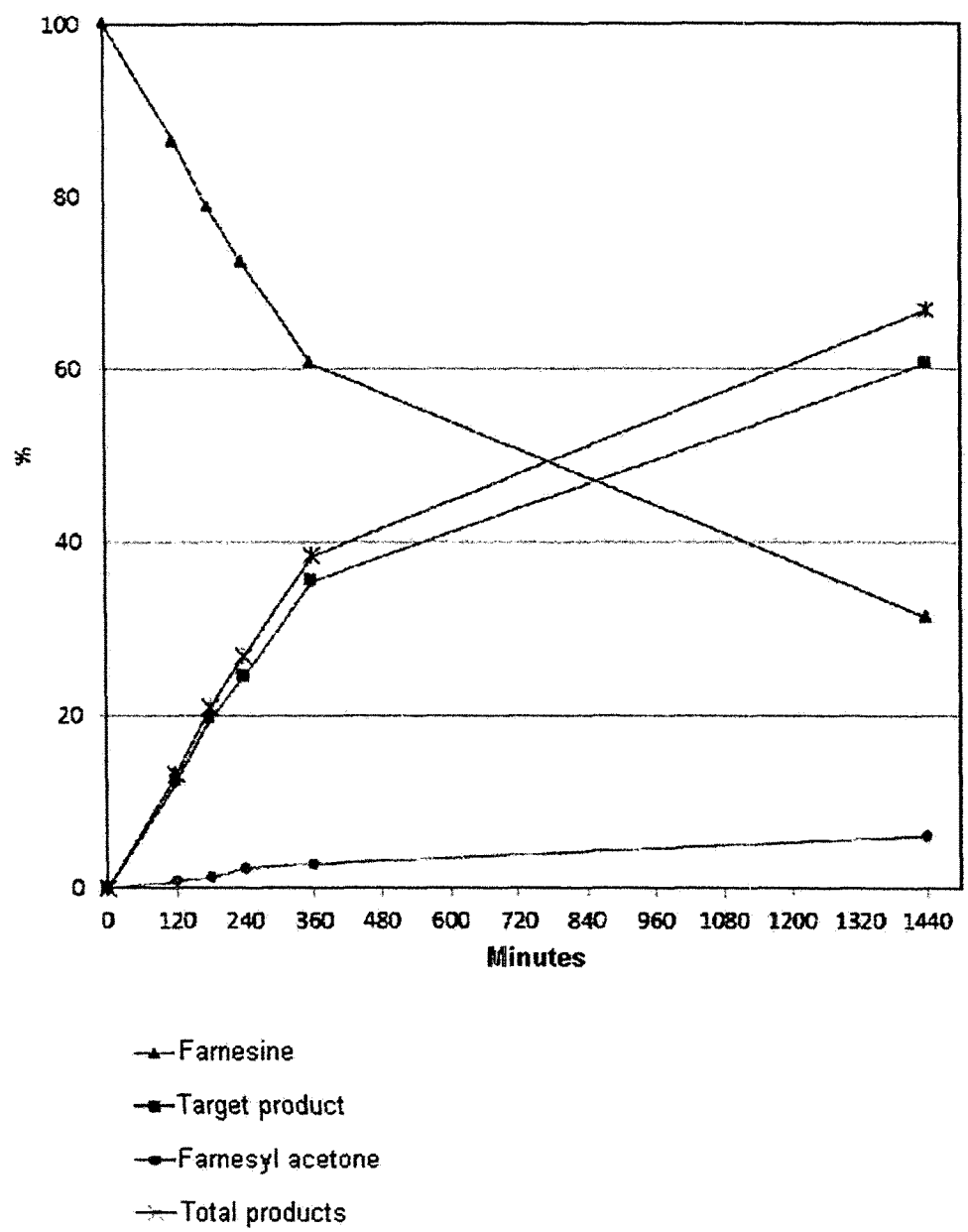
Figure 3:
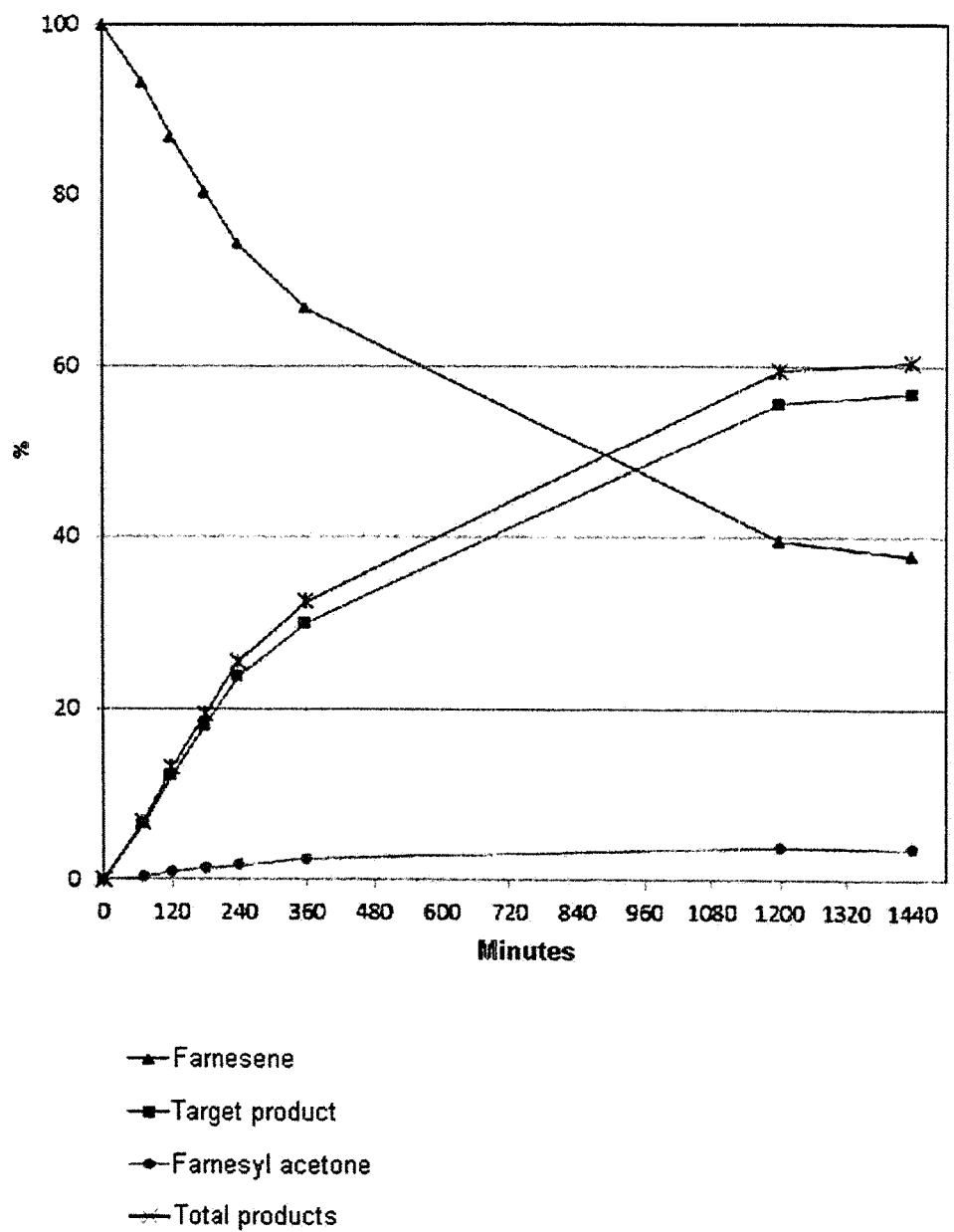
Figure 4:
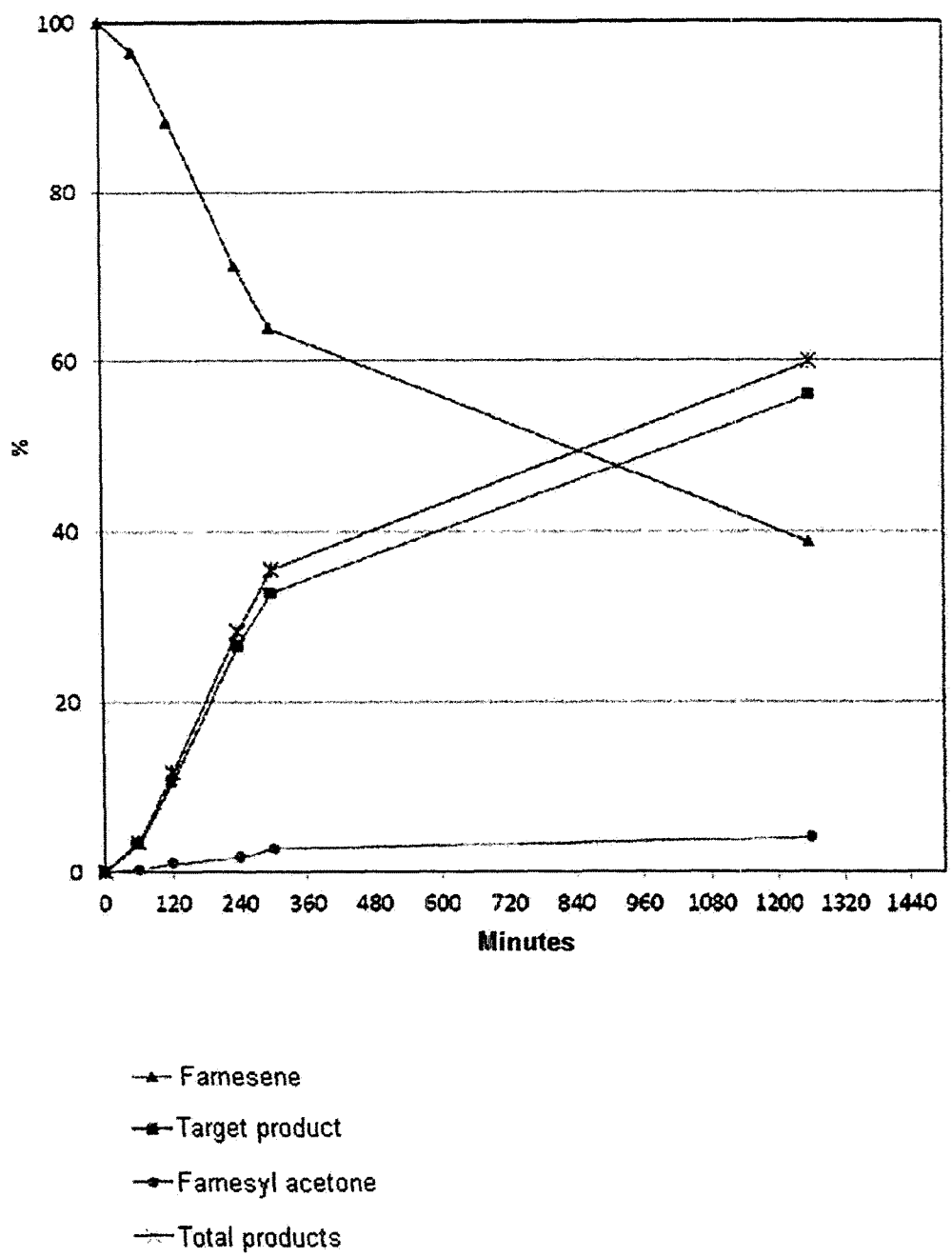
Figure 5:
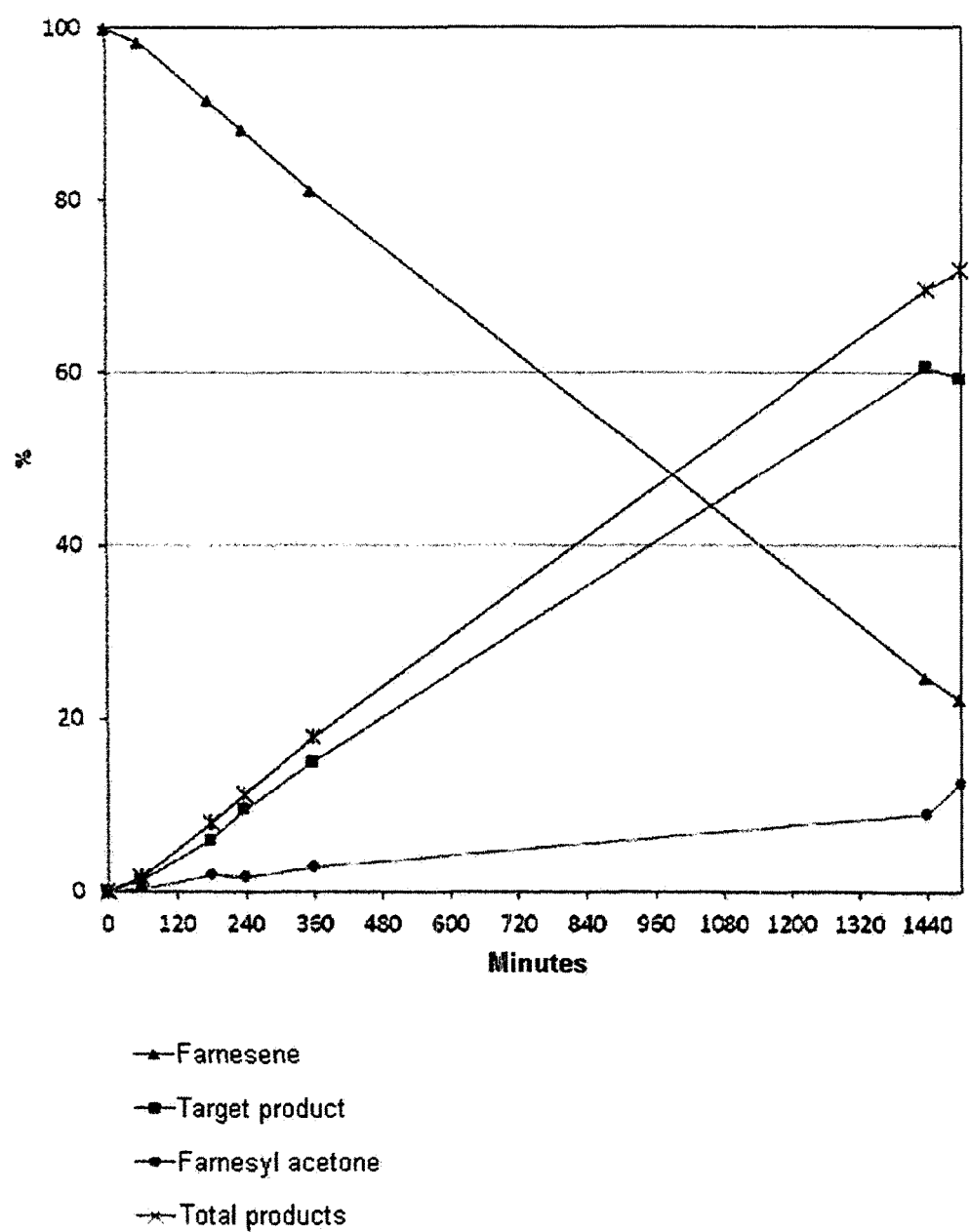
Figure 6:
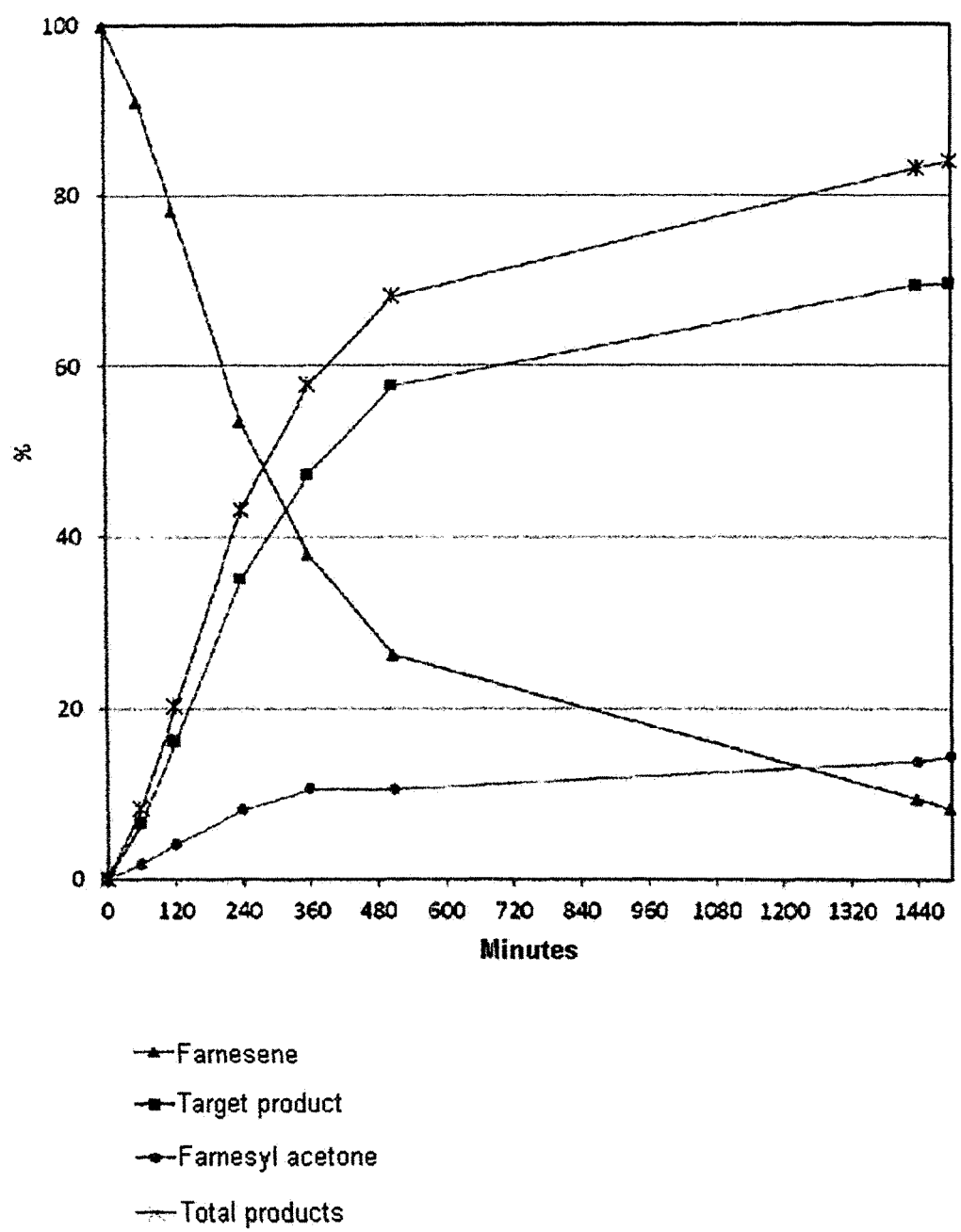
Figure 7:
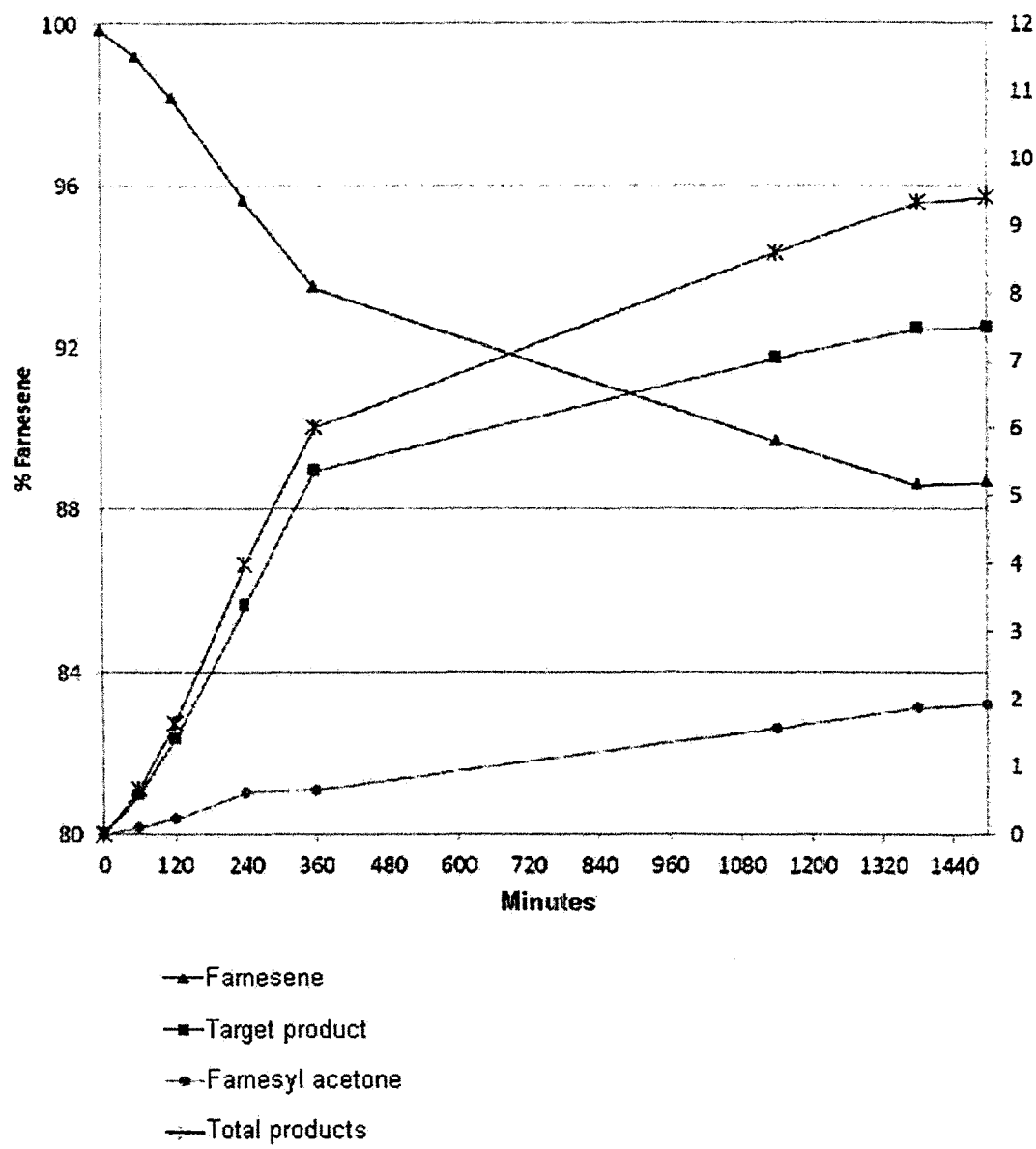
Figure 8:
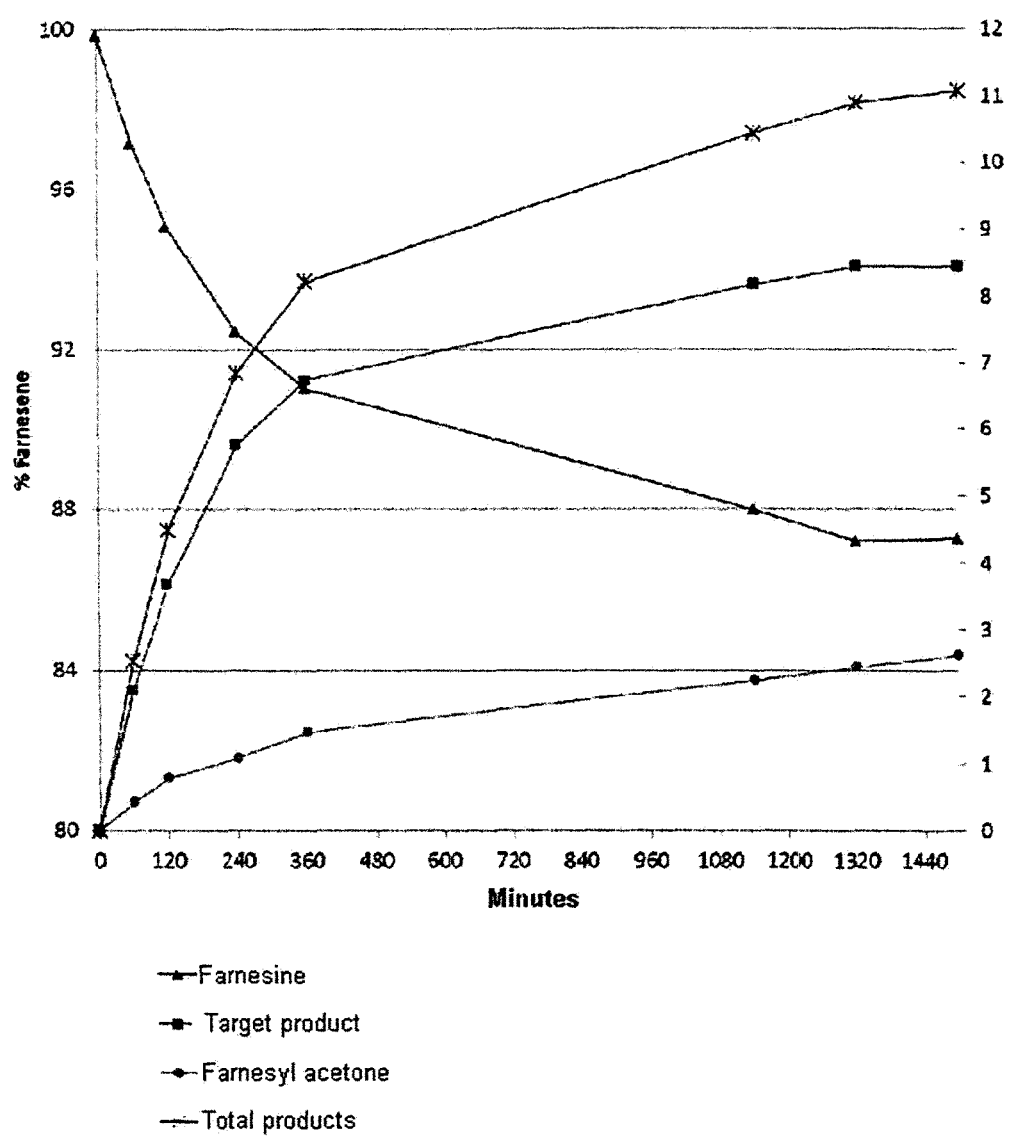
Figure 9:
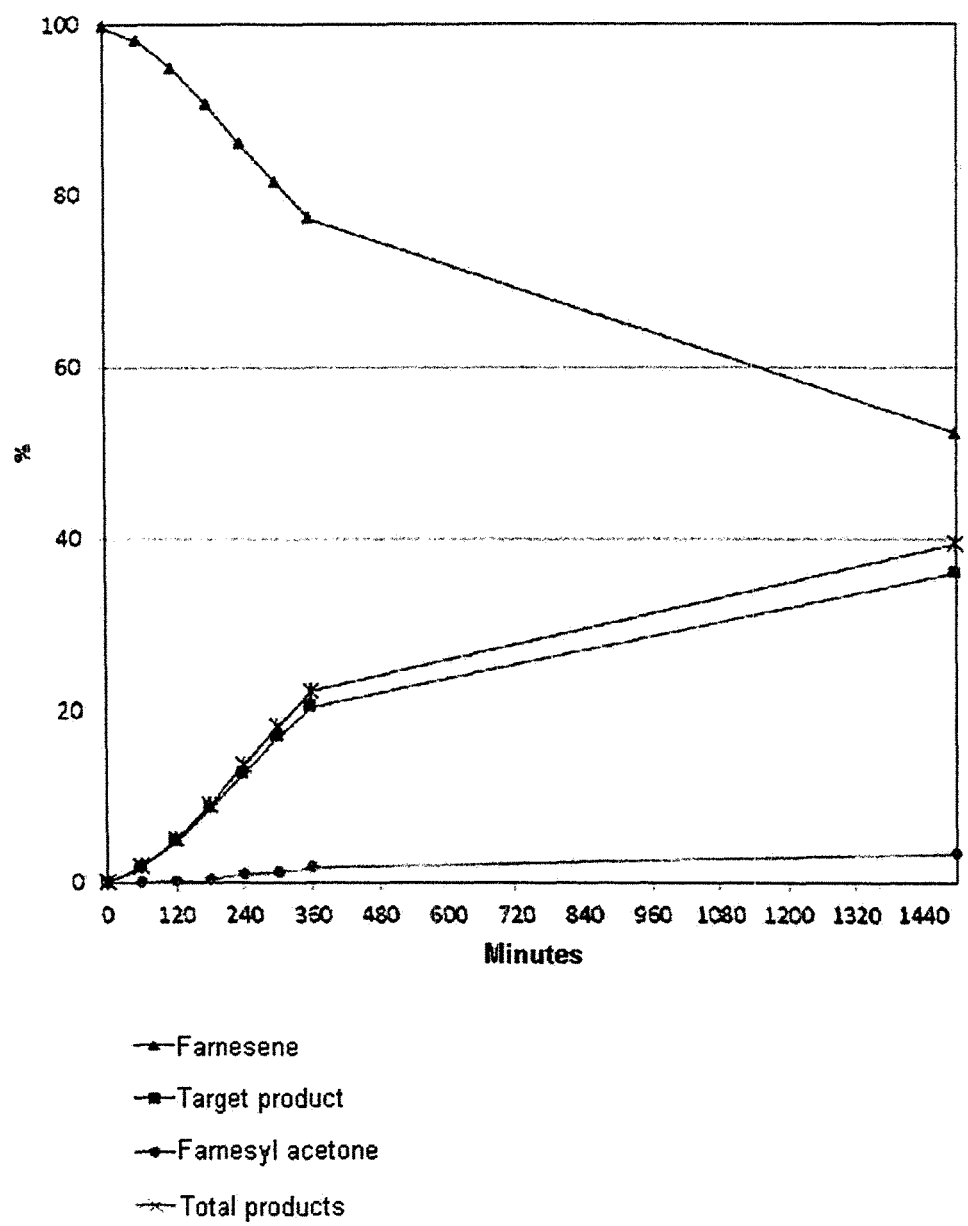

FIG. 1 shows the course of reaction of a process according to the prior art using a solvent mixture of methanol and water in a volume ratio of 3:1, in each case calculated as pure material, with mixing at a stirrer speed of 500 rpm and a power input of 11 W/l, FIG. 2 shows the course of reaction of a process according to the prior art using a solvent mixture of methanol and water in a volume ratio of 1:3, in each case calculated as pure material, with mixing at a stirrer speed of 500 rpm and a power input of 11 W/l, FIG. 3 shows the course of reaction of a process according to the prior art using a solvent mixture of methanol and water in a volume ratio of 1:3, in each case calculated as pure material, with mixing at a stirrer speed of 20 000 rpm and a power input of 662 W/l, FIG. 4 shows the course of reaction of a process according to the prior art using a solvent mixture of methanol and water in a volume ratio of 1:1, in each case calculated as pure material, with mixing at a stirrer speed of 20 000 rpm and a power input of 662 W/l, FIG. 5 shows the course of reaction of the process of the invention using a solvent mixture of ethanol and water in a volume ratio of 1:1 with mixing at a stirrer speed of 500 rpm and a power input of 11 W/l, FIG. 6 shows the course of reaction of the process of the invention using a solvent mixture of ethanol and water in a volume ratio of 1:1, in each case calculated as pure material, with mixing at a stirrer speed of 20 000 rpm and a power input of 662 W/l, FIG. 7 shows the course of reaction of the process of the invention using a solvent mixture of ethanol and water in a volume ratio of 1:1 with mixing at a stirrer speed of 500 rpm and a power input of 11 W/l and using a farnesene isomer mixture as starting material, FIG. 8 shows the course of reaction of the process of the invention using a solvent mixture of ethanol and water in a volume ratio of 1:1, in each case calculated as pure material, with mixing at a stirrer speed of 20 000 rpm and a power input of 662 W/l and using a farnesene isomer mixture as starting material, FIG. 9 shows the course of reaction of a process using water as solvent with mixing at a stirrer speed of 500 rpm and a power input of 11 W/l.

FIG. 1 shows the course of reaction of a process according to the prior art using a solvent mixture of methanol and water in a volume ratio of 3:1, calculated as volume ratio of the pure materials, with mixing at a stirrer speed of 500 rpm and a power input of 11 W/l. The reaction time in minutes is shown on the x axis. The respective composition of the reaction mixture, expressed as % by area of a gas-chromatographic analysis, with certain individual measurements over the course of the reaction is shown on the y axis. Farnesene is represented by a triangle symbol, the target product methyl (4E,8E)-2-acetyl-5,9,13-trimethyltetradeca-4,8,12-trienoate (and isomers thereof), also referred to as X, by a square symbol, farnesyl acetone Y (and isomers thereof) by a circle symbol and the product total by a star symbol.

FIG. 2 shows the course of reaction of a process according to the prior art using a solvent mixture of methanol and water in a volume ratio of 1:3, calculated as volume ratio of the pure materials, with mixing at a stirrer speed of 500 rpm and a power input of 11 W/l. The reaction time in minutes is shown on the x axis. The respective composition of the reaction mixture, expressed as % by area of a gas-chromatographic analysis, with certain individual measurements over the course of the reaction is shown on the y axis. Farnesene is represented by a triangle symbol, the target product methyl (4E,8E)-2-acetyl-5,9,13-trimethyltetradeca-4,8,12-trienoate (and isomers thereof), also referred to as X, by a square symbol, farnesyl acetone Y (and isomers thereof) by a circle symbol and the product total by a star symbol.

FIG. 3 shows the course of reaction of a process according to the prior art using a solvent mixture of methanol and water in a volume ratio of 1:3, calculated as volume ratio of the pure materials, with mixing at a stirrer speed of 20 000 rpm and a power input of 662 W/l, FIG. 4 shows the course of reaction of a process according to the prior art using a solvent mixture of methanol and water in a volume ratio of 1:1, calculated as volume ratio of the pure materials, with mixing at a stirrer speed of 20 000 rpm and a power input of 662 W/l. The reaction time in minutes is shown on the x axis. The respective composition of the reaction mixture, expressed as % by area of a gas-chromatographic analysis, with certain individual measurements over the course of the reaction is shown on the y axis. Farnesene is represented by a triangle symbol, the target product methyl (4E,8E)-2-acetyl-5,9,13-trimethyltetradeca-4,8,12-trienoate (and isomers thereof), also referred to as X, by a square symbol, farnesyl acetone Y (and isomers thereof) by a circle symbol and the product total by a star symbol.

FIGS. 1 and 2 show time/conversion curves according to the prior art. The reaction rate is not significantly increased in the case of faster mixing (high power input), as comparison of Examples A2 and A3 shows. The conversion to the target product is less than 40% after 6 hours reaction time, even at a high power input.

It has surprisingly been found that the reaction rate increases significantly (Example B2) in comparison with the prior art (Example A4) when a specific solvent/water ratio (here ethanol:water=1:1) is set and mixing is then carried out at a high power input.

FIG. 5 shows the course of reaction of the process of the invention using a solvent mixture of ethanol and water in a volume ratio of 1:1 with mixing at a stirrer speed of 500 rpm and a power input of 11 W/l. The reaction time in minutes is shown on the x axis. The respective composition of the reaction mixture, expressed as % by area of a gas-chromatographic analysis, with certain individual measurements over the course of the reaction is shown on the y axis.

Farnesene is represented by a triangle symbol, the target product methyl (4E,8E)-2-acetyl-5,9,13-trimethyltetradeca-4,8,12-trienoate (and isomers thereof), also referred to as X, by a square symbol, farnesyl acetone Y (and isomers thereof) by a circle symbol and the product total by a star symbol.

FIG. 6 shows the course of reaction of the process of the invention using a solvent mixture of ethanol and water in a volume ratio of 1:1 with mixing at a stirrer speed of 20 000 rpm and a power input of 662 W/l. The reaction time in minutes is shown on the x axis. The respective composition of the reaction mixture, expressed as % by area of a gas-chromatographic analysis, with certain individual measurements over the course of the reaction is shown on the y axis.

Farnesene is represented by a triangle symbol, the target product methyl (4E,8E)-2-acetyl-5,9,13-trimethyltetradeca-4,8,12-trienoate (and isomers thereof), also referred to as X, by a square symbol, farnesyl acetone Y (and isomers thereof) by a circle symbol and the product total by a star symbol.

FIG. 7 shows the course of reaction of the process of the invention under the same conditions as in FIG. 5, except that a farnesene isomer mixture was used as starting material. The values, which relate to the conversion and thus to the y axis located at right, are the target product methyl (4E,8E)-2-acetyl-5,9,13-trimethyltetradeca-4,8,12-trienoate (and isomers thereof, square symbol), also referred to as X, farnesyl acetone Y (and isomers thereof, circle symbol), and the product total (star symbol) comprising farnesyl acetone Y (and isomers thereof) and X (and isomers thereof). The farnesene represented by a triangle symbol, on the other hand, is shown on the y axis located at left.

FIG. 8 shows the course of reaction of the process of the invention under the same conditions as in FIG. 6, except that a farnesene isomer mixture was used as starting material. The values, which relate to the conversion and thus to the y axis located at right, are the target product methyl (4E,8E)-2-acetyl-5,9,13-trimethyltetradeca-4,8,12-trienoate (and isomers thereof, square symbol), also referred to as X, farnesyl acetone Y (and isomers thereof, circle symbol), and the product total (star symbol) comprising farnesyl acetone Y (and isomers thereof) and X (and isomers thereof). The farnesene represented by a triangle symbol, on the other hand, is shown on the y axis located at left.

FIG. 9 shows the course of reaction of the process of the invention using water as solvent in a volume ratio of 1:1 with mixing at a stirrer speed of 500 rpm and a power input of 11 W/l. The reaction time in minutes is shown on the x axis. The respective composition of the reaction mixture, expressed as % by area of a gas-chromatographic analysis, with certain individual measurements over the course of the reaction is shown on the y axis.

Farnesene is represented by a triangle symbol, the target product methyl (4E,8E)-2-acetyl-5,9,13-trimethyltetradeca-4,8,12-trienoate (and isomers thereof), also referred to as X, by a square symbol, farnesyl acetone Y (and isomers thereof) by a circle symbol and the product total by a star symbol.

FIG. 9 shows time/conversion curves according to the prior art using pure water as solvent. The reaction rate here is, at the same power input, comparable to the experiments in which ethanol or methanol are added (compare C1 with A2 and B1).

Surprisingly, a specific solvent combination together with at the same time greatly increased power inputs (B 2) thus leads to significantly increased reaction rates, which are necessary for an economical process.

The following examples relate in terms of their designations to the associated figures. The catalytic reaction according to the invention of β-E-farnesene (Bedoukian Res., 90% of β-E-farnesene, >98% total of all farnesene isomers) with methyl acetoacetate as in all examples is shown in scheme 1 below. The product mixture formed in the reaction comprises farnesyl acetone (and isomers thereof), designated by Y (and isomers thereof) and methyl (4E,8E)-2-acetyl-5,9,13-trimethyltetradeca-4,8,12-trienoate (and isomers thereof), designated by X (and isomers thereof). The sum of X and Y is referred to as sum of the products in all figures and examples.

Scheme 1: Schematic depiction of farnesyl acetone (and isomers thereof) designated by Y and methyl (4E, 8E)-2-acetyl-5,9,13-trimethyltetradeca-4,8,12-trienoate (and isomers thereof) designated by X, formed by the catalytic reaction of β-E-farnesene with methyl acetoacetate (AME).

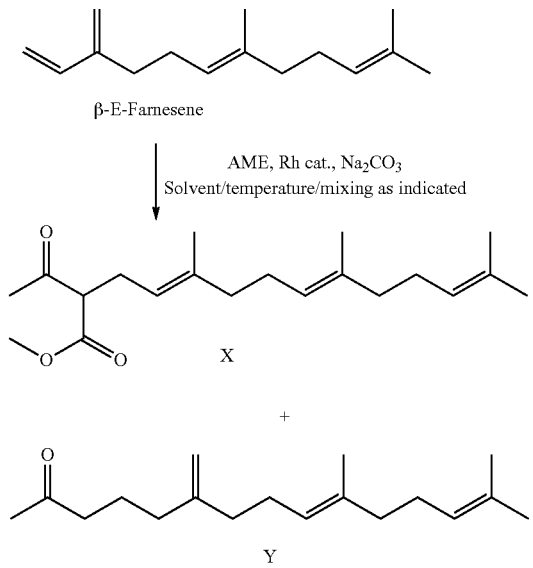

In Examples A1 to C1, chloro(1,5-cyclooctadiene)rhodium(I) dimer (0.07 mmol; 35 mg), trisodium tri(3-sulfonatophenyl)phosphine hydrate (1.1 mmol; 622 mg) and sodium carbonate (0.25 mmol; 26.8 mg) were placed under a protective gas atmosphere in a 250 ml glass flask. Farnesene (trans-β-farnesene or a farnesene isomer mixture corresponding to Table 2, 68.9 mmol; 14.1 g), methyl acetoacetate (170 mmol; 19.7 g) were admixed with water (HPLC grade) and ethanol or methanol in the ratios indicated in Table 2. The substances used are specified further in Table 1. The two-phase mixture was heated while stirring (500 rpm, precision glass stirrer, Teflon stirrer blade having a half-moon shape and a diameter of 7 cm, or an Ultra-Turrax at 20 000 rpm; model IKA T-25 Digital) for 24 hours at an internal temperature of 85° C. The respective reaction conversion was determined by gas-chromatographic analysis at various points in time (sample taken from the dispersed mixture and conversion determined from the organic phase). The gas-chromatographic parameters were: separation column: 60 m*0.25 mm HP5, 1.0 μm film thickness, detector: FID, carrier gas:hydrogen, temp. program; 80° C., 10 min, 20° C./min, 250° C., 30 min; comment: integration is stopped from 0.0 to 9.0 minutes. $t_R$ (farnesenes)=18.5-20 min, $t_R$ (AME)=10.5-12.2 min, $t_R$ (X+isomers)=29.0-32.5 min, $t_R$ (farnesyl acetone Y+isomers)=23.2-25.2 min.

TABLE 1

Overview of the substances used in Examples A1 to D1 and manufacturer's data. no d. means no data.

| No. | Substance | Molar mass | Purity | Manufacturer | CAS number |
|---|---|---|---|---|---|
| 1 | trans-β-Farnesene | 204.35 g/mol | no d. | Bedoukian | 18794-84-8 |
| 2 | Farnesene isomer mixture | 204.35 g/mol | no d. | Sigma-Aldrich | 502-61-4 |
| 3 | Methyl acetoacetate (AME) | 116.12 g/mol | ≥99.0% | Sigma-Aldrich | 105-45-3 |
| 4 | Water (HPLC grade) | 18.01 g/mol | ≥99.0% | J. T. Baker | 7732-18-5 |
| 5 | Ethanol | 46.07 g/mol | ≥94.0% | Alfa Aesar | 64-17-5 |
| 6 | Chloro(1,5-cyclo-octadiene)rhodium(I) dimer | 493.08 g/mol | no d. | no d. | 12092-47-6 |
| 7 | Tri(3-sulfonatophenyl)-phosphine hydrate, sodium salt | 568.40 g/mol | ≥85.0% | Alfa Aesar | 63995-70-0 |
| 8 | Sodium carbonate | 105.99 g/mol | ≥99.8% | Riedel-de Haën | 497-19-8 |

TABLE 2

Overview of the ratios of amounts, rotational speeds of the stirrer and power inputs used in Examples A1 to C1

| Example | Internal temp. [° C.] | rpm | Power input [W/l] | Farnesene | Solvent, volumes |
|---|---|---|---|---|---|
| A1 | 85 | 500 | 11 | trans-β-farnesene | methanol:water = 7.5 ml:2.5 ml |
| A2 | 85 | 500 | 11 | trans-β-farnesene | methanol:water = 2.5 ml:7.5 ml |
| A3* | 85 | 20 000 | 662 | trans-β-farnesene | methanol:water = 3.8 ml:11.2 ml |
| A4* | 85 | 20 000 | 662 | trans-β-farnesene | methanol:water = 7.5 ml:7.5 ml |
| B1 | 85 | 500 | 11 | trans-β-farnesene | ethanol:water = 5 ml:5 ml |
| B2* | 85 | 20 000 | 662 | trans-β-farnesene | ethanol:water = 7.5 ml:7.5 ml |
| B3 | 85 | 500 | 11 | farnesene isomer mixture | ethanol:water = 5 ml:5 ml |
| B4* | 85 | 20 000 | 662 | farnesene isomer mixture | ethanol:water = 7.5 ml:7.5 ml |
| C1 | 85 | 500 | 11 | trans-β-farnesene | Water (10 ml) |

*Batch size of all solvents, volumes and reagents were increased by a factor of 1.5.

Example D1

Conversion of β-E-Farnesene into Hexahydrofarnesyl Acetone

Scheme 2: Schematic depiction of hexahydrofarnesyl acetone formed by catalytic reaction of β-E-farnesene with methyl acetoacetate (AME).

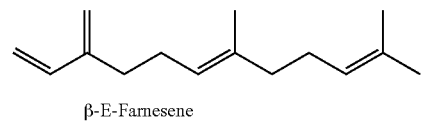

β-E-Farnesene

1. AME, $Na_2CO_3$
   Rh/TPPTS
   $EtOH/H_2O$ 1:1, 18 h, 85° C.
2. 3 h, 180° C., —$CO_2$
3. 10 bar $H_2$, Pd/C, THF, 50° C.

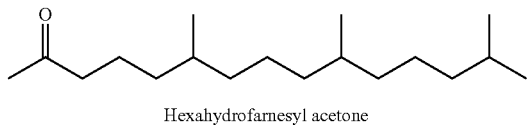

Hexahydrofarnesyl acetone

A reaction output prepared as described in Example B2 (batch size 16.6 mmol; 3.39 g of β-E-farnesene) was allowed to cool to room temperature. The organic phase of the output (yellow, 2-phase) was isolated and the aqueous phase was extracted with toluene (5 ml). The organic phases were combined and the solvent was separated off under reduced pressure at a temperature of 70° C. 4.91 g of a yellow oil were obtained. Water (HPLC grade, 10 ml) was added thereto and the mixture was heated while stirring to a temperature of 180° C. in a 20 ml steel autoclave for 3 hours. A pressure rise to 22 bar absolute occurred. The autoclave was subsequently cooled to room temperature and vented. The output was extracted with toluene (2×6 ml) and the combined organic phases were dried over magnesium sulfate and the solvent was separated off under reduced pressure. 3.54 g of a yellow oil were obtained. The oil obtained was admixed with THF (water-free, 20 ml) and Pd/C (palladium (10%) on activated carbon, Alfa Aeser, 350 mg). The mixture was transferred to a 60 ml steel autoclave and hydrogen (10 bar) was injected. The mixture was heated while stirring to a temperature of 50° C. for 18 hours. The autoclave was then cooled to room temperature and vented. The reaction output (black suspension) was filtered and the solvent was separated off under reduced pressure. This gave 3.50 g of hexahydrofarnesyl acetone as a colorless oil.

Example E1

In Tables 3 and 4 below, the parameters for determining the power input as described above in the description are shown for a rotor-stator stirring system.

TABLE 3

Overview of the parameters for determining the power input of the rotorstator stirring system used (model: IKA T-25 Digital, Ultra-Turrax at 20 000 rpm, carried out using water).

| Mass [kg] | Time [min] | Temp. [° C.] | $cpW_{transverse}$ [kJ/(kg * K)] | $\Delta H_{transverse}$ [kJ/kg] | Density [kg/m$^3$] | Vol. [l] | Temperature rise [° C.] |
|---|---|---|---|---|---|---|---|
| 0.56 | 0 | 22 | 4.188 | 2445.8 | 998.4 | 0.561 | |
| | 5 | 26.9 | | | | | 4.9 |
| | 10 | 33.8 | | | | | 6.9 |
| | 15 | 39.3 | | | | | 5.5 |
| | 21 | 46.3 | | | | | 7 |
| | 25 | 51.7 | | | | | 5.4 |
| | 30 | 57.4 | | | | | 5.7 |
| | 35 | 62 | | | | | 4.6 |
| | 40 | 67.7 | | | | | 5.7 |
| | 45 | 72.7 | | | | | 5 |
| | 51 | 79.4 | | | | | 6.7 |
| | 55 | 83.2 | | | | | 3.8 |
| | 60 | 87.9 | | | | | 4.7 |
| | 65 | 92.8 | | | | | 4.9 |
| | 70 | 96.5 | | | | | 3.7 |
| 0.548 | 74 | 98.7 | 4.218 | 2267.3 | 947.9 | 0.578 | 2.2 |

TABLE 4

Overview of the parameters for determining the power input of a rotor-stator stirring system. Experiment using water

| | | | |
|---|---|---|---|
| Average heat capacity of water | $cpW_{transverse}$ | 4.203 | kJ/(kg*K) |
| Average enthalpy of vaporization of water | $\Delta H_{transverse}$ | 2356.6 | kJ/kg |
| Average density of water | Rho W | 973.2 | kg/m$^3$ |
| Total quantity of heat | q | 206863 | J |
| Power introduced | P | 46.6 | W |
| Initial volume | $V_0$ | 0.56 | l |
| Power input based on initial volume | $P/V_0$ | 83.2 | W/l |
| Rotational speed of rotor | n | 20 000 | /min |
| Diameter of rotor | $d_R$ | 0.018 | m |
| Power index for rotor | Ne | 0.68 | |
| Circumferential velocity of rotor | $v_u$ | 18.85 | m/s |
| Transmission to reaction mixture | | | |
| Density of reaction mixture | ρ | 940 | kg/m$^3$ |
| Volume of reaction mixture | V | 0.068 | l |
| Transmission of stirring power to reaction mixture | P | 45 | W |
| Power input into reaction mixture | P/V | 662 | W/l |

Example E2

Table 5 below shows the parameters for determining the power input of a stirrer system using a half-moon stirrer.

TABLE 5

Overview of the parameters for determining the power input of a stirrer system for a half-moon stirrer. Determination of the power input for the half-moon stirrer

| | | | |
|---|---|---|---|
| Diameter of stirrer | $d_R$ | 0.07 | m |
| Volume of reaction mixture | V | 0.046 | l |
| Density of reaction mixture/system to be stirred | ρ | 940 | kg/m$^3$ |

| Rotational speed | Torque | Stirring power | Power index | Power input | Circumferential velocity |
|---|---|---|---|---|---|

TABLE 5-continued

Overview of the parameters for determining the power input of a stirrer system for a half-moon stirrer. Determination of the power input for the half-moon stirrer

| n [min] | M [Ncm] | P [W] | Ne [—] | P/V [W/l] | v_u [m/s] |
|---|---|---|---|---|---|
| 400 | 0.93 | 0.39 | 0.83 | 8.5 | 1.47 |
| 450 | 0.95 | 0.45 | 0.67 | 9.7 | 1.65 |
| 500 | 0.97 | 0.51 | 0.56 | 11 | 1.83 |
| 550 | 0.99 | 0.57 | 0.47 | 12.4 | 2.02 |
| 600 | 1.01 | 0.63 | 0.4 | 13.8 | 2.2 |

The invention claimed is:

1. A process for preparing keto compounds of the general formula (I)

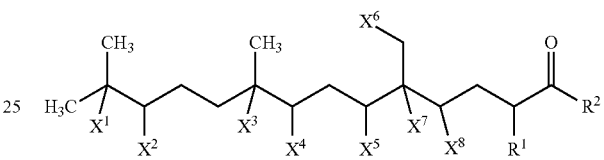

(I)

where
R$^1$ is hydrogen or a —C(O)OR$^3$ radical, where
  R$^3$ is C$_1$-C$_4$-alkyl;
R$^2$ is C$_1$-C$_4$-alkyl;
X$^1$ and X$^2$ are both hydrogen or together are the second bond of a double bond between the carbon atoms to which they are bound;
X$^3$ and X$^4$ are both hydrogen or together are the second bond of a double bond between the carbon atoms to which they are bound;
X$^5$, X$^6$, X$^7$ and X$^8$ are each hydrogen;
where one of the combinations of the radicals X$^5$ and X$^7$, X$^6$ and X$^7$ or X$^7$ and X$^8$ can also be the second bond of a double bond between the carbon atoms to which they are bound, and isomers and mixtures thereof,
where
a) at least one farnesene compound of the general formula (II)

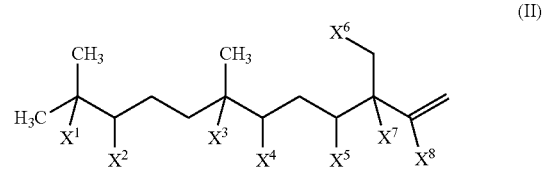

(II)

where
X$^1$ and X$^2$ together are the second bond of a double bond between the carbon atoms to which they are bound;
X$^3$ and X$^4$ together are the second bond of a double bond between the carbon atoms to which they are bound;
X$^5$ and X$^7$ together are the second bond of a double bond between the carbon atoms to which they are bound, with the proviso that X$^6$ is hydrogen; or $X^6$ and $X^7$ together are the second bond of a double bond between the carbon atoms to which they are bound, with the proviso that $X^5$ is hydrogen, and $X^8$ is hydrogen;

is subjected to a reaction with a β-keto ester of the general formula (III)

$R^2$—CO—$CH_2$—$R^1$ (III)

where
$R^1$ is a —C(O)O$R^3$ radical,
where $R^3$ is $C_1$-$C_4$-alkyl
$R^2$ is $C_1$-$C_4$-alkyl;
in the presence of a catalyst wherein the catalyst is a compound or complex of a transition metal of group 9 of the Periodic Table and a solvent/water mixture, where the reaction mixture is subjected to dispersing using at least one mixer at a Reynolds number of greater than $10^4$,
to give a compound of the formula (I-a),

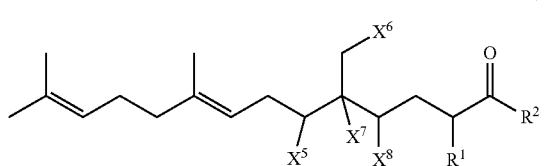

(I-a)

where
$R^1$ is a —C(O)O$R^3$ radical,
where $R^3$ is $C_1$-$C_4$-alkyl;
$R^2$ is $C_1$-$C_4$-alkyl;
$X^1$ and $X^2$ together are the second bond of a double bond between the carbon atoms to which they are bound;
$X^3$ and $X^4$ together are the second bond of a double bond between the carbon atoms to which they are bound;
one of the combinations of the radicals $X^5$ and $X^7$, $X^6$ and $X^7$ or $X^7$ and $X^8$ together is the second bond of a double bond between the carbon atoms to which they are bound and the remaining radicals $X^5$, $X^6$, $X^7$ and $X^8$ are each hydrogen;
and isomers and mixtures thereof;

b) the reaction mixture obtained in step a) is optionally subjected to a decarboxylation to give a compound of the formula (I-b),

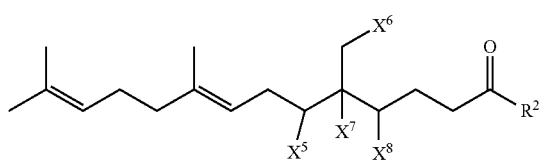

(I-b)

where
$R^2$ is $C_1$-$C_4$-alkyl;
one of the combinations of the radicals $X^5$ and $X^7$, $X^6$ and $X^7$ or $X^7$ and $X^8$ together is the second bond of a double bond between the carbon atoms to which they are bound and the remaining radicals $X^5$, $X^6$, $X^7$ and $X^8$ are each hydrogen;
and isomers and mixtures thereof;

c) the reaction mixture obtained in step b) is optionally subjected to a hydrogenation to give a compound of the formula (I-c)

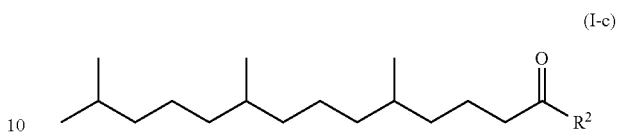

(I-c)

where
$R^2$ is $C_1$-$C_4$-alkyl.

2. The process according to claim 1 for preparing farnesyl acetone of the formula (I-aA),

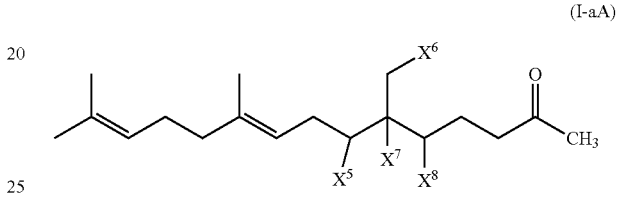

(I-aA)

where
one of the combinations of the radicals $X^5$ and $X^7$, $X^6$ and $X^7$ or $X^7$ and $X^8$ together is the second bond of a double bond between the carbon atoms to which they are bound and the remaining radicals $X^5$, $X^6$, $X^7$ and $X^8$ are each hydrogen,
and isomers and mixtures thereof,
wherein the process comprises the steps a) and b).

3. The process according to claim 1 for preparing hexahydrofarnesyl acetone (6,10,14-trimethyl-2-pentadecanone) of the formula (I-bB),

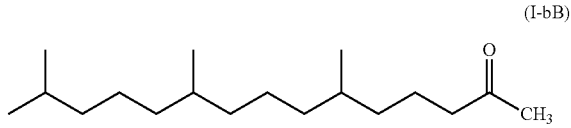 [SMILES: CC(=O)CCCC(C)CCCC(C)CCCC(C)C]

(I-bB)

wherein the process comprises the steps a), b), and c).

4. The process according to claim 1, wherein the solvent of the solvent/water mixture in step a) is selected from among $C_1$-$C_5$-alkanols, $C_2$-$C_6$-dialkanols, saturated cyclic ethers, saturated acyclic ethers, nitriles, saturated ketones, lactams, esters of saturated $C_1$-$C_6$-monocarboxylic acids with $C_1$-$C_6$-alkanols, $C_1$-$C_6$-alkylamides and di-$C_1$-$C_6$-alkylamides of saturated $C_1$-$C_6$-monocarboxylic acids and mixtures thereof.

5. The process according to claim 1, wherein the solvent/water mixture in step a) is present in a volume ratio of from 1:5 to 5:1 calculated as pure material.

6. The process according to claim 1, wherein the solvent/water mixture in step a) is present in a volume ratio of from 2:1 to 1:2 calculated as pure material.

7. The process according to claim 1, wherein the solvent/water mixture in step a) is present in a volume ratio of 1:1 calculated as pure material.

8. The process according to claim 1, wherein dispersing in step a) is carried out at a power input in the range from 0.1 to 5000 W/l.

9. The process according to claim 1, wherein dispersing in step a) is carried out at a power input in the range from 10 to 600 W/l.

10. The process according to claim 1, wherein dispersing in step a) is carried out at a power input in the range from 20 to 100 W/l.

11. The process according to claim 1, wherein dispersing in step a) is carried out using a stirrer at a circumferential velocity in the range from 1 to 80 m/s.

12. The process according to claim 1, wherein dispersing in step a) is carried out using a stirrer at a circumferential velocity in the range from 1.8 to 30 m/s.

13. The process according to claim 1, wherein dispersing in step a) is carried out at a temperature in the range from 50 to 200° C.

14. The process according to claim 1, wherein dispersing in step a) is carried out at a temperature in the range from 60 to 150° C.

15. The process according to claim 1, wherein dispersing in step a) is carried out at a temperature in the range from 70 to 120° C.

16. A process for preparing vitamin E, isophytol, dehydroisophytol, hexahydrofarnesyl acetone or tetrahydrofarnesyl acetone which comprises utilizing the farnesyl acetone obtainable by the process as defined in claim 1.

17. The process according to claim 1, wherein the catalyst is a rhodium compound or a rhodium complex.

18. The process according to claim 1, wherein the catalyst is rhodium(I), rhodium(II), rhodium(III) chloride, rhodium(III) bromide, rhodium(III) nitrate, rhodium(III) sulfate, rhodium(II) or rhodium(III) oxide, rhodium(II) or rhodium(III) acetate, rhodium(II) or rhodium(III) carboxylate, $Rh(CH_3COCH_2COCH_3)_3$, dicarbonyl-rhodium acetylacetonate, $[RhCl(cycloocta-1,5-diene)]_2$, $[RhCl(CO)_2]_2$ or $RhCl_3(C_2H_5NH_2)_3$.

19. The process according to claim 1, wherein the catalyst is $[RhCl(cycloocta-1,5-diene)]_2$.

* * * * *